United States Patent [19]

Shuman et al.

[11] 4,322,340
[45] Mar. 30, 1982

[54] PHARMACOLOGICALLY ACTIVE PEPTIDES

[75] Inventors: Robert T. Shuman, Greenwood; Paul D. Gesellchen, Indianapolis, both of Ind.

[73] Assignee: Eli Lilly and Company, Indianapolis, Ind.

[21] Appl. No.: 198,900

[22] Filed: Oct. 20, 1980

[51] Int. Cl.³ ........................................... C07C 103/52
[52] U.S. Cl. ............................................... 260/112.5 E
[58] Field of Search .................................. 260/112.5 E

[56] References Cited

FOREIGN PATENT DOCUMENTS

| 870819 | 3/1979 | Belgium | 260/112.5 R |
| 770579 | 2/1977 | South Africa | 260/112.5 R |
| 774479 | 7/1977 | South Africa | 260/112.5 R |

OTHER PUBLICATIONS

Life Science vol. 23, pp. 1371–1378.
Vitamins & Hormones 36, 297–382 (1978).
Effects of Enkephalin Analogues on Prolactin Release in the Rat (1978).

*Primary Examiner*—Delbert R. Phillips
*Attorney, Agent, or Firm*—William C. Martens, Jr.; Arthur R. Whale

[57] ABSTRACT

Compounds of the formula

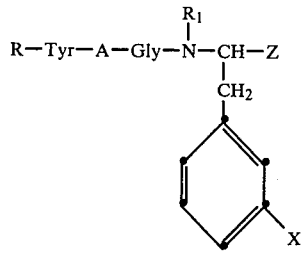

and pharmaceutically acceptable non-toxic acid addition salts thereof, in which R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me) (O), Ser, Thr, and Hse;

$R_1$ is $C_1$–$C_3$ primary alkyl, cyclopropylmethyl, allyl, ethylthiomethyl, 2-fluoroethyl, or propargyl;

X is bromo, iodo, chloro, methyl, trifluoromethyl, or methoxy; and

Z is —CH$_2$OR$_2$,

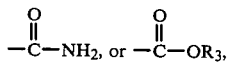

in which $R_2$ is hydrogen, acetyl, or acetoxymethyl and $R_3$ is $C_1$–$C_3$ alkyl; are useful analgesic agents.

39 Claims, No Drawings

PHARMACOLOGICALLY ACTIVE PEPTIDES

BACKGROUND OF THE INVENTION

This invention relates to a novel class of compounds which exhibit analgesic activity.

Recently, endogenous substances having morphine-like properties have been extracted from mammalian brain or csf. These substances, named enkephalin, have been identified by Hughes et al., *Nature*, 258, 577 (1975) as pentapeptides having the following sequences:

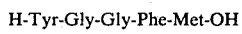

H-Tyr-Gly-Gly-Phe-Met-OH

H-Tyr-Gly-Gly-Phe-Leu-OH.

These compounds are referred to as methionine-enkephalin and leucine-enkephalin, respectively.

Although methionine and leucine enkephalin have been shown to exhibit analgesic activity in mice upon administration intracerebroventricularly [Buscher et al., *Nature*, 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., *Life Sciences* 21, pp. 559–562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide;

(c) modification of the Phe in the 4-position by α-aza substitution, N-methylation, or hydrogenation of the aromatic ring.

In addition, Roemer et al., *Nature* 268, pp. 547–549 (1977), suggest modification of the Met[5] to its corresponding carbinol and oxidation of the Met sulfur to the sulfoxide as useful modifications.

Another structural modification of significance is that reported in Belgian Pat. No. 859,026. This publication suggests enhancement of activity and bioavailability of enkephalin analogs by insertion of a D-amino acid residue in position 2, conversion of the terminal carboxyl to an amide, and N-alkylation of the amino acid residue in position 5.

A class of analogs of enkephalin having a high level of analgesic activity coupled with low physical dependence liability has now been discovered. These analogs are tetrapeptides having a ring-substituted phenylalanine. They are highly specific in terms both of the identity and the position of the substitution. In particular, they are tetrapeptides having the residue of a meta-substituted L-phenylalanine in the 4-position of the peptide.

The literature recognizes other ring-substituted 4-phenylalanyl enkephalin analogs; however, they are not meta-substituted 4-phenylalanyl enkephalin analogs. A. R. Day et al., *Res. Comm. in Chem. Path. and Pharmacol.* 14 (4), 597–603 (1976) reports H-Tyr-Gly-Gly-pClPhe-Nle-OH. R. J. Miller et al., *Vitamins and Hormones* 36, 297–382, Academic Press (1978) mentions H-Tyr-D-Ala-Gly-pClPhe-D-Leu-OH; H-Tyr-D-Ala-Gly-p-ClPhe-D-Leu-OMe; and H-Tyr-D-Ala-Gly-p-ClPhe-D-Leu-NHEt. Pless et al., "Opioid Activity of Enkephalin Analogues," presented at the 15th European Peptide Symposium, Sept. 4–9, 1978, Gdansk, Poland, reports H-Tyr-D-Ala-Gly-pClPhe-Met(O)-OL. D. H. Coy et al., *BBRC* 83 (3), 977–983 (1978) mentions H-Tyr-D-Ala-Gly-F$_5$Phe-Met-NH$_2$. South African Pat. No. 77/0579 generically discloses pentapeptide enkephalin analogs variously substituted on the ring of the phenylalanine residue. U.S. application Ser. No. 104,529 filed Dec. 17, 1979, discloses and claims tetrapeptide enkephalin analogs containing a p-fluoro substituted phenylalanine.

None of the above reports the compounds of this invention, and it has been discovered that both the identity and the position of the substituent on the L-phenylalanine play a significant role both in the level of analgesic activity and the degree of physical dependence liability of the enkephalin analog.

SUMMARY OF THE INVENTION

Thus, this invention relates to a class of compounds having the formula

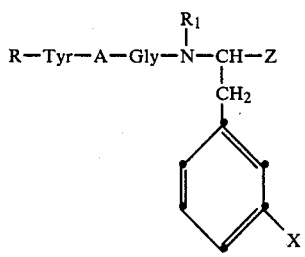

and pharmaceutically acceptable non-toxic acid addition salts thereof, in which

R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me)(O), Ser, Thr, and Hse;

R$_1$ is C$_1$–C$_3$ primary alkyl, cyclopropylmethyl, allyl, ethylthiomethyl, 2-fluoroethyl, or propargyl;

X is bromo, iodo, chloro, methyl, trifluoromethyl, or methoxy; and

Z is —CH$_2$OR$_2$,

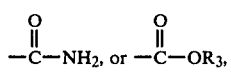

in which R$_2$ is hydrogen, acetyl, or acetoxymethyl, and R$_3$ is C$_1$–C$_3$ alkyl.

DETAILED DESCRIPTION OF THE INVENTION

As indicated above, the compounds of this invention have the following structure:

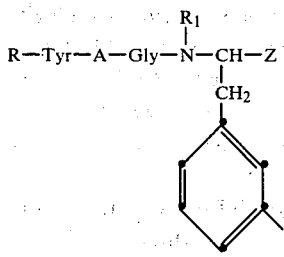

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are tetrapeptides, the C-terminal portion of which is a primary alcohol or its ether derivative, a primary amide, or a lower alkyl ester.

The stereoconfiguration of the compounds of this invention is an essential feature thereof. For the sake of convenience, the amino acid residues of the tetrapeptides of this invention are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists.

The group $R_1$ as used herein as defined to include the group "$C_1$-$C_3$ primary alkyl". By the term "$C_1$-$C_3$ primary alkyl" is meant methyl, ethyl, and n-propyl.

The group $R_3$ as used herein is defined to include the group "$C_1$-$C_3$ alkyl". By the term "$C_1$-$C_3$ alkyl" is intended methyl, ethyl, n-propyl and isopropyl.

With respect to the particular position residues of the tetrapeptides of this invention, the following considerations prevail:

(A). Position 1

This position represents the amino-terminal portion of the peptide. The residue is that which results from L-tyrosine. The residue can be N-unsubstituted, in which case R is hydrogen. Moreover, the residue can be N-mono-substituted, giving rise to N-methyl, N-ethyl-, N-cyclopropylmethyl-, or N-allyl-. For compounds having exceptionally high levels of analgesic activity when administered parenterally, the tyrosyl residue which is present in Position 1 preferably is N-unsubstituted. For compounds having exceptionally high levels of analgesic activity when administered orally, the tyrosyl residue preferably is N-substituted. In the event that the tyrosyl is N-substituted, the N-substituent preferably is methyl.

(B). Position 2.

The amino acid residue (A) which is present in the second position of the peptides of this invention must be the D stereoisomer and is any of several α-amino acid residues depending upon the substitutent ($R_4$) on the α-carbon. These include residues derived from D-alanine (Ala) ($R_4$ is methyl), D-α-aminobutyric acid (Abu) ($R_4$ is ethyl), D-norvaline (Nva) ($R_4$ is n-propyl), D-valine (Val) ($R_4$ is isopropyl), D-norleucine (Nle) ($R_4$ is n-butyl), D-leucine (Leu) ($R_4$ is isobutyl), D-isoleucine (Ile) ($R_4$ is sec-butyl), D-allylglycine [Gly(Al)] ($R_4$ is allyl), D-cyclopropylmethylglycine [Gly(Cp)] ($R_4$ is cyclopropylmethyl), D-methionine (Met) ($R_4$ is 2-methylthioethyl), D-(S-methyl)cysteine [Cys(Me)] ($R_4$ is methylthiomethyl), D-methionine sulfoxide [Met(O)] ($R_4$ is methylsulfinylethyl), D-(S-methyl)cysteine sulfoxide [Cys(Me)(O)] ($R_4$ is methylsulfinylmethyl), D-serine (Ser) ($R_4$ is hydroxymethyl), D-threonine (Thr) ($R_4$ is 1-hydroxyethyl), and D-homoserine (Hse) ($R_4$ is 2-hydroxyethyl). Preferably, A is Ala, Abu, Nva, Val, Nle, Leu, Ile, Ser, Thr, or Hse, and, more preferably, is Ala, Abu, Nva, Val, Nle, Leu, or Ile. Most preferably, A is Ala.

(C). Position 3.

The amino acid residue present in this position is that derived from glycine (Gly).

(D). Position 4

The amino acid residue present in this position is that derived from meta-substituted L-phenylalanine [Phe(X)]. The residue is substituted at the amino nitrogen ($R_1$) with methyl, ethyl, n-propyl, cyclopropylmethyl, allyl, ethylthiomethyl, 2-fluoroethyl, or propargyl. Preferably, $R_1$ is $C_1$-$C_3$ primary alkyl, allyl, cyclopropylmethyl, or propargyl. Most preferably, $R_1$ is ethyl, cyclopropylmethyl, allyl, or propargyl.

In addition, the L-phenylalanine moiety is ring-substituted at the meta position. The substituent can be any of bromo, iodo, chloro, methyl, trifluoromethyl, or methoxy. Preferably, the substituent is bromo or iodo, and, most preferably, is bromo.

The L-phenylalanine is the C-terminal residue of the compounds of this invention and is an amino acid structurally derivatized to is amide

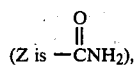

(Z is $-CNH_2$), its primary alcohol or ether derivative

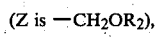

(Z is $-CH_2OR_2$), or its $C_1$-$C_3$ alkyl ester

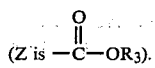

(Z is $-C-OR_3$).

Preferably, the residue is derivatized to its primary amide, its alcohol, or its ester derivative. Of the above, the primary amide is most preferred.

In this specification, the following abbreviations, most of which are well known and are commonly used in the art, are employed:

Abu—α-aminobutyric acid
Ala—alanine
Cys—cysteine
Cys(Me)—(S-methyl)cysteine
Cys(Me)(O)—(S-methyl)cysteine sulfoxide
Gly—glycine
Gly(Al)—allylglycine Gly(Cp)—cyclopropylmethylglycine
Hse—homoserine
Ile—isoleucine
Leu—leucine
Met—methionine
Met(O)—methionine sulfoxide
Nle—norleucine
Nva—norvaline
Phe—phenylalanine
Ser—serine
Thr—threonine
Tyr—tyrosine
Val—valine
Ac—acetyl
AcOMe—acetoxymethyl
Al—allyl
Cp—cyclopropylmethyl
Me—methyl
Et—ethyl
Ip-isopropyl
Pr—n-propyl
OMe—methoxy
Etm—ethylthiomethyl
Fle-2-fluoroethyl
Ppg—propargyl
Bu—n-butyl
i-Bu—isobutyl
t-Bu—t-butyl
s-Bu—sec-butyl
Boc—t-butyloxycarbonyl
Bzl—benzyl
Cbz—benzyloxycarbonyl
DCC—N,N′-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl
NMM—N-methylmorpholine
IBCF—isobutyl chloroformate 18-crown-6—1,4,7,10,13,16-hexaoxacyclooctadecane Examples of typical compounds of this invention include the following, each of which carries a substituent in the meta position of the phenylalanine and any or all of which may be in the form of a pharmaceutically acceptable non-toxic acid addition salt:

H-L-Tyr-D-Ala-Gly-L-(N-Me)Phe(Br)-NH$_2$;
H-L-Tyr-D-Ala-Gly-L-(N-Et)Phe(I)-NH$_2$;
H-L-Tyr-D-Abu-Gly-L-(N-Pr)Phe(Br)-NH$_2$;
H-L-Tyr-D-Abu-Gly-L-(N-Et)Phe(Br)-NH$_2$;
H-L-Tyr-D-Nva-Gly-L-(N-Ppg)Phe(Me)-NH$_2$;
H-L-Tyr-D-Nva-Gly-L-(N-Et)Phe(OMe)-NH$_2$;
H-L-Tyr-D-Val-Gly-L-(N-Et)Phe(CF$_3$)-NH$_2$;
H-L-Tyr-D-Val-Gly-L-(N-Pr)Phe(Cl)-NH$_2$;
H-L-Tyr-D-Nle-Gly-L-(N-Cp)Phe(I)-NH$_2$;
H-L-Tyr-D-Nle-Gly-L-(N-Ppg)Phe(Br)-NH$_2$;
H-L-Tyr-D-Leu-Gly-L-(N-Etm)Phe(Br)-NH$_2$;
H-L-Tyr-D-Leu-Gly-L-(N-Cp)Phe(OMe)-NH$_2$;
H-L-Tyr-D-Ile-Gly-L-(N-Al)Phe(Br)-NH$_2$;
H-L-Tyr-D-Ile-Gly-L-(N-Cp)Phe(Me)-NH$_2$;
H-L-Tyr-D-Ala-Gly-L-(N-Et)Phe(CF$_3$)-NH$_2$;
H-L-Tyr-D-Ala-Gly-L-(N-Pr)Phe(OMe)-NH$_2$;
H-L-Tyr-D-Ala-Gly-L-(N-Fle)Phe(Cl)-NH$_2$;
H-L-Tyr-D-Ala-Gly-L-(N-Etm)Phe(I)-NH$_2$;
H-L-Tyr-D-Ala-Gly-L-(N-Fle)Phe(I)-NH$_2$;
H-L-Tyr-D-Ala-Gly-L-(N-Etm)Phe(Br)-NH$_2$;
H-L-Tyr-D-Ala-Gly-L-(N-Cp)Phe(Br)-NH$_2$;
H-L-Tyr-D-Ala-Gly-L-(N-Al)Phe(I)-NH$_2$;
H-L-Tyr-D-Ala-Gly-L-(N-Ppg)Phe(OMe)-NH$_2$;
H-L-Tyr-D-Thr-Gly-L-(N-Cp)Phe(Me)-NH$_2$;
H-L-Tyr-D-Val-Gly-L-(N-Et)Phe(CF$_3$)-NH$_2$;
H-L-Tyr-D-Leu-Gly-L-(N-Et)Phe(Br)-NH$_2$;
H-L-Tyr-D-Val-Gly-L-(N-Al)Phe(Br)-NH$_2$;
H-L-Tyr-D-Leu-Gly-L-(N-Al)Phe(Cl)-NH$_2$;
H-L-Tyr-D-Thr-Gly-L-(N-Cp)Phe(CF$_3$)-NH$_2$;
H-L-Tyr-D-Thr-Gly-L-(N-Et)Phe(OMe)-NH$_2$;
H-L-Tyr-D-Thr-Gly-L-(N-Me)Phe(Br)-NH$_2$;
H-L-Tyr-D-Thr-Gly-L-(N-Pr)Phe(Br)-NH$_2$;
H-L-Tyr-D-Thr-Gly-L-(N-Al)Phe(Cl)-NH$_2$;
H-L-Tyr-D-Gly(Al)-Gly-L-(N-Et)Phe(Me)-NH$_2$;
H-L-Tyr-D-Gly(Cp)-Gly-L-(N-Me)Phe(OMe)-NH$_2$;
H-L-Tyr-D-Met-Gly-L-(N-Et)Phe(CF$_3$)-NH$_2$;
H-L-Tyr-D-Cys(Me)-Gly-L-(N-Cp)Phe(Br)-NH$_2$;
H-L-Tyr-D-Met(O)-Gly-L-(N-Pr)Phe(Br)-NH$_2$;
H-L-Tyr-D-Cys(Me)(O)-Gly-L-(N-Cp)Phe(Br)-NH$_2$;
H-L-Tyr-D-Ser-Gly-L-(N-Cp)Phe(I)-NH$_2$;
H-L-Tyr-D-Ser-Gly-L-(N-Et)Phe(Cl)-NH$_2$;
(N-Me)-L-Tyr-D-Ala-Gly-L-(N-Cp)Phe(Br)-NH$_2$;
(N-Me)-L-Tyr-D-Thr-Gly-L-(N-Et)Phe(I)-NH$_2$;
H-L-Tyr-D-Hse-Gly-L-(N-Cp)Phe(Br)-NH$_2$;
(N-Me)-L-Tyr-D-Ala-Gly-L-(N-Et)Phe(Br)-NH$_2$;
(N-Me)-L-Tyr-D-Ala-Gly-L-(N-Me)Phe(Br)-NH$_2$;
(N-Me)-L-Tyr-D-Ala-Gly-L-(N-Pr)Phe(Br)-NH$_2$;
(N-Et)-L-Tyr-D-Abu-Gly-L-(N-Cp)Phe(I)-NH$_2$;
(N-Me)-L-Tyr-D-Val-Gly-L-(N-Et)Phe(Me)-NH$_2$;
(N-Pr)-L-Tyr-D-Leu-Gly-L-(N-Cp)Phe(CF$_3$)-NH$_2$;
H-L-Tyr-D-Abu-Gly-L-(N-Al)Phe(OMe)-NH$_2$;
H-L-Tyr-D-Nle-Gly-L-(N-Al)Phe(Br)-NH$_2$;
H-L-Tyr-D-Ile-Gly-L-(N-Ppg)Phe(Br)-NH$_2$;
(N-Me)-L-Tyr-D-Leu-Gly-L-(N-Et)Phe(Br)-NH$_2$;
(N-Me)-L-Tyr-D-Nva-Gly-L-(N-Me)Phe(Br)-NH$_2$;
(N-Me)-L-Tyr-D-Ala-Gly-L-(N-Ppg)Phe(I)-NH$_2$;
(N-Et)-L-Tyr-D-Ala-Gly-L-(N-Me)Phe(Br)-NH$_2$;
(N-Cpm)-L-Tyr-D-AlaGly-L-(N-Me)Phe(Cl)-NH$_2$;
(N-Me)-L-Tyr-D-Ala-Gly-L-(N-Cp)Phe(Br)-NH$_2$;
(N-Al)-L-Tyr-D-Ala-Gly-L-(N-Al)Phe(Br)-NH$_2$;
(N-Me)-L-Tyr-D-Ala-Gly-L-(N-Etm)Phe(Br)-NH$_2$;
(N-Et)-L-Tyr-D-Ala-Gly-L-(N-Et)Phe(I)-NH$_2$;
(N-Cpm)-L-Tyr-D-Ala-Gly-L-(N-Et)Phe(Me)-NH$_2$;
(N-Me)-L-Tyr-D-Ala-Gly-L-(N-Al)Phe(OMe)-NH$_2$;
H-L-Tyr-D-Ala-Gly-L-(N-Me)Phe(I)-CH$_2$OH;
H-L-Tyr-D-Ala-Gly-L-(N-Et)Phe(Cl)-CH$_2$OH;
H-L-Tyr-D-Abu-Gly-L-(N-Cp)Phe(Br)-CH$_2$OH;
H-L-Tyr-D-Abu-Gly-L-(N-Et)Phe(Br)-CH$_2$OH;
H-L-Tyr-D-Nva-Gly-L-(N-Cp)Phe(OMe)-CH$_2$OH;
H-L-Tyr-D-Nva-Gly-L-(N-Et)Phe(CF$_3$)-CH$_2$OH;
H-L-Tyr-D-Val-Gly-L-(N-Cp)Phe(Br)-CH$_2$OH;
H-L-Tyr-D-Val-Gly-L-(N-Pr)Phe(I)-CH$_2$OH;
H-L-Tyr-D-Nle-Gly-L-(N-Cp)Phe(OMe)-CH$_2$OH;
H-L-Tyr-D-Nle-Gly-L-(N-Ppg)Phe(Br)-CH$_2$OH;
H-L-Tyr-D-Leu-Gly-L-(N-Etm)Phe(I)-CH$_2$OH;
H-L-Tyr-D-Leu-Gly-L-(N-Cp)Phe(Me)-CH$_2$OH;
H-L-Tyr-D-Ile-Gly-L-(N-Al)Phe(OMe)-CH$_2$OH;
H-L-Tyr-D-Ile-Gly-L-(N-Cp)Phe(CF$_3$)-CH$_2$OH;
H-L-Tyr-D-Ala-Gly-L-(N-Et)Phe(Br)-CH$_2$OH;
H-L-Tyr-D-Ala-Gly-L-(N-Pr)Phe(Br)-CH$_2$OH;
H-L-Tyr-D-Ala-Gly-L-(N-Fle)Phe(I)-CH$_2$OH;
H-L-Tyr-D-Ala-Gly-L-(N-Etm)Phe(Cl)-CH$_2$OH;
H-L-Tyr-D-Ala-Gly-L-(N-Fle)Phe(I)-CH$_2$OH;
H-L-Tyr-D-Ala-Gly-L-(N-Fle)Phe(Br)-CH$_2$OH;
H-L-Tyr-D-Ala-Gly-L-(N-Cp)Phe(Me)-CH$_2$OH;
H-L-Tyr-D-Ala-Gly-L-(N-Al)Phe(CF$_3$)-CH$_2$OH;
H-L-Tyr-D-Ala-Gly-L-(N-Ppg)Phe(OMe)-CH$_2$OH;
H-L-Tyr-D-Thr-Gly-L-(N-Et)Phe(Br)-CH$_2$OH;

H-L-Tyr-D-Val-Gly-L-(N-Et)Phe(Br)-CH₂OH;
H-L-Tyr-D-Leu-Gly-L-(N-Et)Phe(Br)-CH₂OH;
H-L-Tyr-D-Val-Gly-L-(N-Al)Phe(I)-CH₂OH;
H-L-Tyr-D-Leu-Gly-L-(N-Al)Phe(Br)-CH₂OH;
H-L-Tyr-D-Thr-Gly-L-(N-Cp)Phe(Br)-CH₂OH;
H-L-Tyr-D-Thr-Gly-L-(N-Et)Phe(Me)-CH₂OH;
H-L-Tyr-D-Thr-Gly-L-(N-Me)Phe(OMe)-CH₂OH;
H-L-Tyr-D-Thr-Gly-L-(N-Pr)Phe(CF₃)-CH₂OH;
H-L-Tyr-D-Thr-Gly-L-(N-Al)Phe(Br)-CH₂OH;
H-L-Tyr-D-Gly(AL)-Gly-L-(N-Cp)Phe(Cl)-CH₂OH;
H-L-Tyr-D-Gly(Cp)-Gly-L-(N-Me)Phe(Br)-CH₂OH;
H-L-Tyr-D-Met-Gly-L-(N-Et)Phe(I)-CH₂OH;
H-L-Tyr-D-Cys(Me)-Gly-L-(N-Cp)Phe(Br)-CH₂OH;
H-L-Tyr-D-Met(O)-Gly-L-(N-Pr)Phe(Br)-CH₂OH;
H-L-Tyr-D-Cys(Me)(O)-Gly-L-(N-Cp)Phe(Me)-CH₂OH;
H-L-Tyr-D-Ser-Gly-L-(N-Cp)Phe(Br)-CH₂Oh;
H-L-Tyr-D-Ser-Gly-L-(N-Et)Phe(Br)-CH₂OH;
(N-Me)-L-Tyr-D-Ala-Gly-L-(N-Cp)Phe(Br)-CH₂OH;
(N-Me)-L-Tyr-D-Thr-Gly-L-(N-Et)Phe(Br)-CH₂OH;
H-L-Tyr-D-Hse-Gly-L-(N-Et)Phe(I)-CH₂OH;
(N-Me)-L-Tyr-D-Ala-Gly-L-(N-Et)Phe(Me)-CH₂OH;
(N-Me)-L-Tyr-D-Ala-Gly-L-(N-Me)Phe(OMe)-CH₂OH;
(N-Me)-L-Tyr-D-Ala-Gly-L-(N-Pr)Phe(CF₃)-CH₂OH;
(N-Et)-L-Tyr-D-Abu-Gly-L-(N-Cp)Phe(Cl)-CH₂OH;
(N-Me)-L-Tyr-D-Val-Gly-L-(N-Et)Phe(Br)-CH₂OH;
(N-Pr)-L-Tyr-D-Leu-Gly-L-(N-Cp)Phe(Br)-CH₂OH;
H-L-Tyr-D-Abu-Gly-L-(N-Al)Phe(I)-CH₂OH;
H-L-Tyr-D-Nle-Gly-L-(N-Al)Phe(OMe)-CH₂OH;
H-L-Tyr-D-Ile-Gly-L-(N-Ppg)Phe(CF₃)-CH₂OH;
(N-Me)-L-Tyr-D-Leu-Gly-L-(N-Et)Phe(Br)-CH₂OH;
(N-Me)-L-Tyr-D-Nva-Gly-L-(N-Me)Phe(Br)-CH₂OH;
(N-Me)-L-Tyr-D-Ala-Gly-L-(N-Ppg)Phe(I)-CH₂OH;
(N-Et)-L-Tyr-D-Ala-Gly-L-(N-Me)Phe(Br)-CH₂OH;
(N-Cpm)-L-Tyr-D-AlaGly-L-(N-Me)Phe(CF₃)-CH₂OH;
(N-Me)-L-Tyr-D-Ala-Gly-L-(N-Cp)Phe(OMe)-CH₂OH;
(N-Al)-L-Tyr-D-Ala-Gly-L-(N-Al)Phe(Me)-CH₂OH;
(N-Me)-L-Tyr-D-Ala-Gly-L-(N-Fle)Phe(Br)-CH₂OH;
(N-Et)-L-Tyr-D-Ala-Gly-L-(N-Et)Phe(Br)-CH₂OH;
(N-Al)-L-Tyr-D-Ala-Gly-L-(N-Et)Phe(Cl)-CH₂OH;
(N-Me)-L-Tyr-D-Ala-Gly-L-(N-Al)Phe(I)-CH₂OH;
H-L-Tyr-D-Ala-Gly-L-(N-Et)Phe(Br)-CH₂OAc;
H-L-Tyr-D-Ala-Gly-L-(N-Et)Phe(Br)-CH₂OAcOMe;
H-L-Tyr-D-Ala-Gly-L-(N-Me)Phe(I)-CH₂OAcOMe;
H-L-Tyr-D-Ala-Gly-L-(N-Me)Phe(Me)-CH₂OAc;
H-L-Tyr-D-Ala-Gly-L-(N-Et)Phe(OMe)-CH₂OAcOMe;
H-L-Tyr-D-Ala-Gly-L-(N-Al)Phe(CF₃)-CH₂OAcOMe;
H-L-Tyr-D-Ala-Gly-L-(N-Pr)Phe(Br)-CH₂OAc;
H-L-Tyr-D-Ala-Gly-L-(N-Cp)Phe(Br)-CH₂OAc;
H-L-Tyr-D-Ala-Gly-L-(N-Al)Phe(Br)-CH₂OAc;
H-L-Tyr-D-Ala-Gly-L-(N-Me)Phe(I)-OMe;
H-L-Tyr-D-Ala-Gly-L-(N-Cp)Phe(Br)-OEt;
H-L-Tyr-D-Abu-Gly-L-(N-Cp)Phe(Br)-OMe;
H-L-Tyr-D-Abu-Gly-L-(N-Et)Phe(Br)-OMe;
H-L-Tyr-D-Nva-Gly-L-(N-Et)Phe(OMe)-OPr;
H-L-Tyr-D-Nva-Gly-L-(N-Et)Phe(CF₃)-OIp;
H-L-Tyr-D-Val-Gly-L-(N-Cp)Phe(Me)-OMe;
H-L-Tyr-D-Val-Gly-L-(N-Pr)Phe(Br)-OEt;
H-L-Tyr-D-Nle-Gly-L-(N-Cp)Phe(Cl)-OEt;
H-L-Tyr-D-Nle-Gly-L-(N-Pr)Phe(Br)-OMe;
H-L-Tyr-D-Leu-Gly-L-(N-Etm)Phe(I)-OEt;
H-L-Tyr-D-Leu-Gly-L-(N-Cp)Phe(Br)-OPr;
H-L-Tyr-D-Ile-Gly-L-(N-Et)Phe(Br)-OMe;
H-L-Tyr-D-Ile-Gly-L-(N-Al)Phe(Me)-OMe;
H-L-Tyr-D-Ala-Gly-L-(N-Et)Phe(OMe)-OMe;
H-L-Tyr-D-Ala-Gly-L-(N-Pr)Phe(CF₃)-OEt;
H-L-Tyr-D-Ala-Gly-L-(N-Al)Phe(Br)-OIp;
H-L-Tyr-D-Ala-Gly-L-(N-Fle)Phe(Br)-OMe;
H-L-Tyr-D-Ala-Gly-L-(N-Cp)Phe(Br)-OMe;
H-L-Tyr-D-Ala-Gly-L-(N-Etm)Phe(Br)-OEt;
H-L-Tyr-D-Ala-Gly-L-(N-Ppg)Phe(I)-OPr;
H-L-Tyr-D-Ala-Gly-L-(N-Fle)Phe(Me)-OIp;
(N-Me)-L-Tyr-D-Ala-Gly-L-(N-Et)Phe(OMe)-OMe;
(N-Me)-L-Tyr-D-Ala-Gly-L-(N-Me)Phe(CF₃)-OMe;
H-L-Tyr-D-Val-Gly-L-(N-Et)Phe(Br)-OMe;
H-L-Tyr-D-Leu-Gly-L-(N-Et)Phe(Cl)-OEt;
H-L-Tyr-D-Val-Gly-L-(N-Me)Phe(Br)-OMe;
H-L-Tyr-D-Leu-Gly-L-(N-Me)Phe(Br)-OEt;
H-L-Tyr-D-Ala-Gly-L-(N-Cp)Phe(I)-OPr;
(N-Me)-L-Tyr-D-Ala-Gly-L-(N-Et)Phe(Br)-OIp;
(N-Et)-L-Tyr-D-Ala-Gly-L-(N-Et)Phe(Br)-OMe;
(N-Me)-L-Tyr-D-Ala-Gly-L-(N-Al)Phe(Cl)-OMe;
(N-Me)-L-Tyr-D-Ala-Gly-L-(N-Al)Phe(I)-OEt;
H-L-Tyr-D-Gly(Al)-Gly-L-(N-Et)Phe(Br)-OEt;
H-L-Tyr-D-Gly(Cp)-Gly-L-(N-Et)Phe(Me)-OPr;
H-L-Tyr-D-Met-Gly-L-(N-Me)Phe(OMe)-OMe;
H-L-Tyr-D-Cys(Me)-Gly-L-(N-Et)Phe(CF₃)-OPr;
H-L-Tyr-D-Met(O)-Gly-L-(N-Cp)Phe(Br)-OIp;
H-L-Tyr-D-Cys(Me)(O)-Gly-L-(N-Cp)Phe(Br)-OMe;
H-L-Tyr-D-Ser-Gly-L-(N-Me)Phe(Br)-OEt;
(N-Al)-L-Tyr-D-Ala-Gly-L-(N-Et)Phe(I)-OEt;
H-L-Tyr-D-Thr-Gly-L-(N-Me)Phe(Br)-OEt;
H-L-Tyr-D-Thr-Gly-L-(N-Et)Phe(Br)OMe;
H-L-Tyr-D-Hse-Gly-L-(N-Et)Phe(Me)-OMe;
(N-Me)-L-Tyr-D-Thr-Gly-L-(N-Et)Phe(OMe)-OMe;
H-L-Tyr-D-Thr-Gly-L-(N-Al)Phe(CF₃)-OMe;
(N-Me)-L-Tyr-D-Ala-Gly-L-(N-Me)Phe(Br)-OMe;
(N-Et)-L-Tyr-D-Abu-Gly-L-(N-Cp)Phe(Br)-OEt;
(N-Me)-L-Tyr-D-Val-Gly-L-(N-Et)Phe(Br)-OMe;
(N-Cpm)-L-Tyr-D-Leu-Gly-L-(N-Et)Phe(Br)-OMe;
H-L-Tyr-D-Abu-Gly-L-(N-Al)Phe(Br)-OMe;
(N-Me)-L-Tyr-D-Nle-Gly-L-(N-Et)Phe(I)-OEt;
H-L-Tyr-D-Ile-Gly-L-(N-Pr)Phe(Cl)-OPr;
(N-Me)-L-Tyr-D-Leu-Gly-L-(N-Fle)Phe(Me)-OIp;
(N-Me)-L-Tyr-D-Nva-Gly-L-(N-Etm)Phe(Br)-OIp;
(N-Me)-L-Tyr-D-Met-Gly-(N-Et)Phe(Br)-OPr;
H-L-Tyr-D-Ser-Gly-L-(N-Me)Phe(I)-OMe;
H-L-Tyr-D-Nle-Gly-L-(N-Me)Phe(Br)-OEt;
H-L-Tyr-D-Ile-Gly-L-(N-Et)Phe(Br)-OMe;
(N-Me)-L-Tyr-D-Met-Gly-L-(N-Al)Phe(Br)-OMe;
(N-Me)-L-Tyr-D-Val-Gly-L-(N-Pr)Phe(Br)-OMe;
H-L-Tyr-D-Gly(Al)-Gly-L-(N-Me)Phe(Br)-OMe;
(N-Me)-L-Tyr-D-Gly(Cp)-Gly-L-(N-Et)Phe(Br)-OMe;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized by solid phase peptide synthesis or by classical solution phase synthesis. In the solid phase method, the peptide chain is sequentially constructed using a resin support, typically a p-methylbenzhydrylamine resin or a chloromethylated polystyrene resin. The product is cleaved from the resin with HF and purified, generally chromatographically.

Whichever method is used, the preparation of the compounds of this invention involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A more complete discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of an unprotected tyrosyl residue.

A preferred specific method for preparing the compounds of this invention involves coupling a dipeptide representing the amino acid residues in the 2- and 3- positions with the C-terminal amino acid following which the resulting tripeptide is coupled to the N-terminal tyrosine. The C-terminal amino acid can be structured so as to contain the amide, alcohol, ether, or ester moiety. Alternatively, it can contain a group which represents a precursor to the desired C-terminal moiety. The general sequence is depicted by the scheme provided hereinbelow. In the sequence, the letter Z represents the C-terminal moiety, whether in its final form or as a precursor, the symbol AA represents an amino acid residue, and the number appended to the symbol AA represents the position of the amino acid in the ultimate peptide product sequence.

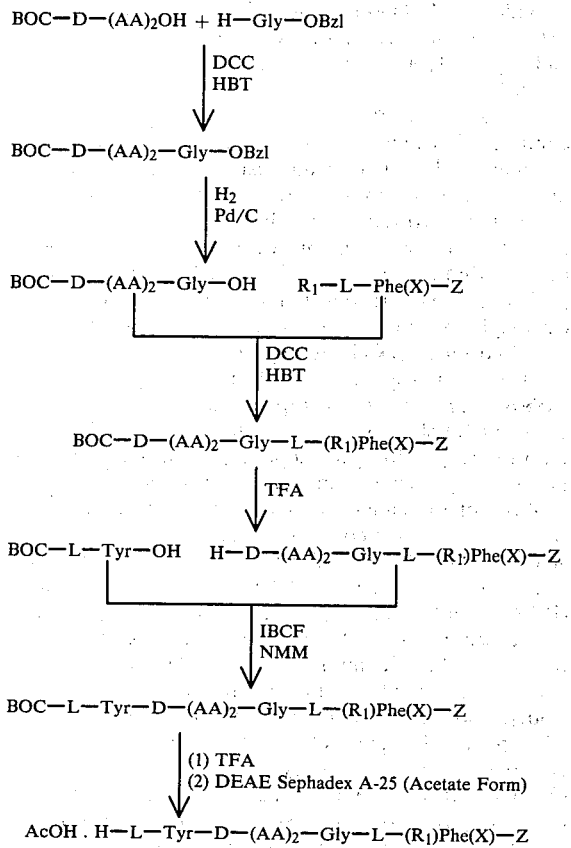

The above represents only one sequence for preparing compounds of this invention. Other sequences, of course, are available. One involves coupling a separately prepared N-terminal tripeptide with a separately prepared C-terminal amino acid followed by appropriate deblocking of any remaining blocked moieties. Another solution method which can be employed involves the step-wise, sequential addition of single amino acids in construction of the peptide chain beginning with the C-terminal amino acid moiety. Reaction techniques such as those described above are employed in this as well as any other contemplated preparative sequence.

In certain of the compounds of this invention, one or more of the groups R and $R_1$ are, variously, alkyl, allyl, propargyl, ethylthiomethyl, 2-fluoroethyl, or cyclopropylmethyl. In these instances, the appropriate N-substituted amino acid is employed in the preparative sequence. Any of the N-monosubstituted amino acids can be prepared as follows using an N-protected amino acid as starting material:

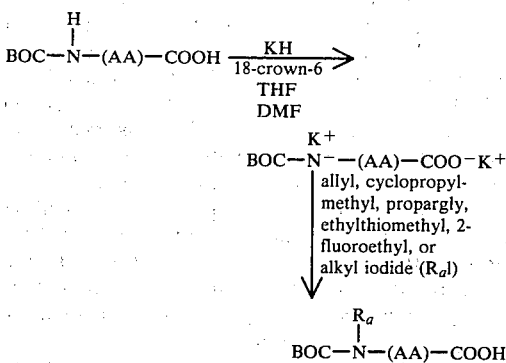

As the above sequence indicates, the amino acid first is treated with potassium hydride in the presence of a suitable crown ether to generate the dianion. The intermediate then is treated with the appropriate allyl, cyclopropylmethyl, propargyl, ethylthiomethyl, 2-fluoroethyl, or alkyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even if excessive racemization does occur, the product can be purified by recrystallization as the salt of d(+) α-phenylethylamine.

The C-terminal portion of the peptides of this invention is derivatized to its primary amide, ester, alcohol, or ether. Derivatization to the amide is accomplished by activation of the carboxyl group of the amino acid with N,N'-dicyclohexylcarbodiimide (DCC) in the presence of 1-hydroxybenzotriazole (HBT) to give the HBT ester. The ester then is reacted with anhydrous ammonia to give the amide.

The C-terminal esters are available from the corresponding acids by techniques well recognized in the art. Derivatization to the primary alcohol is achieved by preparing the methyl ester of the C-terminal amino acid or peptide. The ester then is reduced using sodium borohydride and lithium chloride to give the corresponding primary alcohol derivative.

The ethers can be prepared by any of a variety of well-recognized methods. One involves treating the corresponding alcohol in an aqueous sodium hydroxide medium with an alkyl bromide in which the alkyl group corresponds to the intended alkyl portion of the ether product.

The compounds of this invention are valuable pharmaceutical agents. They exhibit analgesic activity and also neuroleptic activity. They are especially useful in alleviation of pain and amelioration of emotional disturbances when administered parenterally or orally to mammals, including humans. An added highly significant benefit of the compounds of this invention is that, in conjunction with their analgesic and neuroleptic activity, they exhibit very low physical dependence liability.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispensing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 0.5 $\mu$g. to about 2 mg. per kilogram body weight of the recipient, and, preferably, from about 10 $\mu$g. to about 100 $\mu$g. per kilogram body weight, when administered intramuscularly or subcutaneously, and from about 0.1 $\mu$g. to about 200 $\mu$g. per kilogram body weight of the recipient, and, preferably, from about 1 $\mu$g. to about 50 $\mu$g. per kilogram body weight, when administered intravenously. When administered orally, the dosage generally will range from about 100 $\mu$g. to about 100 mg. per kilogram body weight of the recipient, and, preferably, from about 500 $\mu$g. to about 50 mg. per kilogram body weight, and, more preferably, from about 1 mg. to about 10 mg. per kilogram body weight.

The following examples are provided to illustrate the preparation and activity of the compounds of this invention. They are not intended to be limiting upon the scope thereof.

EXAMPLE 1—Preparation of L-(N-Methyl)tyrosyl-D-alanyl-glycyl-L-(N-cyclopropylmethyl)-m-bromophenylalanine Amide, Acetate Salt A. $N^\alpha$-Acetyl-$\beta$-cyano-D,L-m-bromophenylalanine, ethyl ester To a mechanically stirred suspension of 16.8 grams (0.35 m.) of sodium hydride (50% in mineral oil) in 260 ml. of dry THF at room temperature were added in small portions 59.56 grams (0.35 m.) of ethyl acetamidocyanoacetate. A solution of 87.48 grams (0.35 m.) of m-bromobenzyl bromide in 50 ml. of THF (dry) was added dropwise to the reaction mixture. The mixture was first cooled slightly and then was allowed to stir at room temperature for 72 hours after which it was refluxed for 4 hours. The mixture then was cooled to room temperature, and 80 ml. of ethyl alcohol were added. The mixture was stirred for an additional 30 minutes and then was poured onto 1 N HCl. The aqueous mixture was extracted with ethyl acetate, and the ethyl acetate layer was separated and washed successively with water, 1 N sodium bicarbonate, and water. The ethyl acetate was dried over magnesium sulfate and concentrated in vacuo to an oil (107 grams).

NMR $\delta$ 2.0 (acetyl), 3.4–3.5 (methylene) and 7.1–7.5 (m-bromophenyl).

B. D,L-m-Bromophenylalanine

The product from Part A (107 grams; 0.32 m.) was suspended in a solution of 58.8 grams (1.47 m.) of sodium hydroxide pellets and 220 ml. of water. The resulting mixture was refluxed for 24 hours. The mixture then was cooled to room temperature, and the pH was adjusted to 6.5 with 6 N HCl. The resulting precipitate was collected and dried to give 41.01 grams (53%) of the title compound.

C. $N^\alpha$-Trifluoroacetyl-D,L-m-bromophenylalanine

To 200 ml. of trifluoroacetic acid were added 46.53 grams (0.19 m.) of D,L-m-bromophenylalanine. The mixture was cooled to 0° C., and 29.3 ml. (0.21 m.) of trifluoroacetic anhydride were added over a period of five minutes. The resulting solution was stirred at 0° C. for 1.5 hours. The mixture was stirred for three hours at room temperature after which it was concentrated in vacuo. The residue was diluted with 400 ml. of water, and the resulting precipitate was collected and dried. The solid was crystallized from a mixture of ether and petroleum ether to give 28.4 grams (44%) of the title compound.

Analysis, calculated for $C_{11}H_9NO_3BrF_3$ (340.1): C, 38.85; H, 2.67; N, 4.12. Found: C, 39.09; H, 2.46; N, 4.32.

D. L-m-Bromophenylalanine

To 500 ml. of water were added 28 grams (0.082 m.) of the product from Part C. The mixture was stirred, and 2 N NaOH was added until a clear solution (pH 7.2) was obtained. Carboxypeptidase A (25 mg.) was added, and the solution was maintained at 37° C. by a thermostatically-controlled water bath and at pH 7.2 by a Radiometer pH-stat. After five days of gentle stirring, the solution was adjusted to pH 5.0, carbon was added, and the mixture filtered. The filtrate was adjusted to pH 3.0 with 1 N HCl and extracted three times with ethyl acetate. The aqueous solution then was adjusted to pH 7.0 with 2 N NaOH and concentrated in vacuo until the L isomer began to crystallize. The mixture then was allowed to cool to room temperature. The resulting precipitate was collected and dried to give 10.9 grams (109%) of the title compound.

E. $N^\alpha$-t-Butyloxycarbonyl-L-m-bromophenylalanine

To a mixture of 25 ml. of t-butyl alcohol and 20 ml. of water were added 9.9 grams (0.041 m.) of the product from Part D followed by 20.5 ml. (0.041 m.) of 2 N NaOH and 8.9 grams (0.041 m.) of di-t-butyl carbonate. The mixture was stirred at room temperature for five hours after which 150 ml. of water were added. The aqueous mixture was extracted with ether. The aqueous layer then was acidified to pH 2.5 with cold 1 N HCl and extracted with ether. The ether layer was extracted with water, dried over magnesium sulfate, and evaporated in vacuo to an oil. The oil was dissolved in petroleum ether and allowed to stand at 4° C. overnight. The resulting crystals were collected and dried to give 11.3 grams (80%) of the title compound, m.p. 124°–125° C. $[\alpha]_D^{25}$ +16.7° (c=1.0, EtOH).

Analysis, calculated for $C_{14}H_{18}NO_4Br$ (344): C, 48.85; H, 5.27; N, 4.07. Found: C, 49.25; H, 5.59; N, 4.04.

F. $N^\alpha$-t-Butyloxycarbonyl-L-m-bromophenylalanine Amide

To 50 ml. of DMF were added 11.5 grams (0.033 m.) of $N^\alpha$-t-butyloxycarbonyl L-m-bromophenylalanine. The mixture was cooled to −15° C., and 3.63 ml. (0.033 m.) of NMM and 4.33 ml. (0.33 m.) of isobutyl chloroformate were added. The mixture was stirred at −15° C. for five minutes after which anhydrous ammonia (gas) was bubbled into the reaction mixture of one hour. The mixture was stirred for an additional four hours at −15° C. The mixture then was poured onto a mixture of crushed ice and 1 N sodium bicarbonate. The resulting aqueous solution was extracted with ethyl acetate. The organic layer was separated and extracted successively with water, 1.5 N citric acid, and water. The organic phase was dried over magnesium sulfate and concentrated in vacuo to a solid. The solid was triturated with ether, and the resulting precipitate was collected and dried to give 11.3 grams (100%) of the title compound, m.p. 146°–147° C.

$[\alpha]_D^{25}$ +9.8° (c=0.5, MeOH).

Analysis, calculated for $C_{14}H_{19}N_2O_3Br$ (343.2): C, 48.99; H, 5.58; N, 8.16. Found: C, 48.85; H, 5.33; N, 7.91.

G. L-m-Bromophenylalanine Amide, Hydrochloride Salt

To 60 ml. of freshly prepared 1 N HCl (gas) in glacial acetic acid containing 5 ml. of anisole were added 11.1 grams (0.032 m.) of the product from Part F. The mixture was stirred at room temperature for 30 minutes. The mixture then was poured into ether, and the resulting precipitate was collected and dried to give 8.75 grams (98%) of the title compound.

$[\alpha]_D^{25}$ +13.46° (c=0.5, MeOH).

Analysis, calculated for $C_9H_{12}N_2OClBr$ (279.6): C, 38.67; H, 4.33; N, 10.02. Found: C, 38.55; H, 4.41; N, 10.00.

H. $N^\alpha$-Cyclopropylmethyl-L-m-bromophenylalanine Amide

To 50 ml. of anhydrous ethanol were added 4.2 grams (0.015 m.) of the product from Part G followed by 5.04 grams (0.06 m.) of solid anhydrous sodium bicarbonate and 2.04 grams (0.015 m.) of cyclopropylmethyl bromide. The mixture was refluxed for seven hours. The mixture then was evaporated in vacuo to an oil. The oil was dissolved in 20 ml. of chloroform and applied to a 3×40 cm. column of Grace and Davison grade 62 silica gel in chloroform. The product was eluted with a step gradient of up to 10% methanol. The product was isolated according to the thin layer profile of the fractions collected to give 2.2 grams (49%) of the title compound.

NMR δ 1.6 (—NH—), and 7.0–7.4 (m-bromophenyl).

I. $N^\alpha$-t-Butyloxycarbonyl-D-alanyl-glycyl-L-($N^\alpha$-cyclopropylmethyl)-m-bromophenylalanine Amide To 40 ml. of DMF were added 2.1 grams (7.1 mmoles) of the product from Part H. The mixture was cooled to 0° C., and 1.87 grams (7.1 mmoles) of $N^\alpha$-t-butyloxycarbonyl-D-alanyl-glycine were added followed by 0.96 grams (7.1 mmoles) of HBT and 1.46 grams (7.1 mmoles) of DCC. The mixture was stirred at 0° C. for four hours, and then at room temperature for 72 hours. The mixture then was cooled to 0° C., the resulting precipitates were removed by filtration, and filtrate was evaporated in vacuo. The residue was dissolved in ethyl acetate, and the solution was extracted successively with 1 N sodium bicarbonate, water, 1.5 N citric acid, and water. The organic phase then was dried over magnesium sulfate and evaporated in vacuo to an oil to give 1.5 grams (40%) of the title compound.

J. $N^\alpha$-t-Butyloxycarbonyl-$N^\alpha$-methyl-L-tyrosyl-D-alanyl-glycyl-L-($N^{60}$-cyclopropylmethyl)-m-bromophenylalanine Amide To 50 ml. of trifluoroacetic acid containing 5 ml. of anisole were added 1.5 grams (2.9 mmoles) of the product from Part I. The mixture was stirred at 0° C. for 30 minutes and was evaporated in vacuo without heat. The resulting oil was diluted with ether. The supernate was decanted, and the remaining oil was dried in vacuo.

To 15 ml. of DMF were added 0.856 grams (2.9 mmoles) of $N^\alpha$-t-butyloxycarbonyl-$N^\alpha$-methyl-L-tyrosine. The mixture was cooled to −15° C., and 0.32 ml. (2.9 mmoles) of NMM and 0.38 ml. (2.9 mmoles) of IBCF were added rapidly to the stirred solution. Stirring was continued at −15° C. during the preparation of the following:

The TFA salt of the tripeptide from above was dissolved in 10 ml. of DMF. The mixture was cooled to 0° C., and 0.32 ml. (2.9 mmoles) of NMM was added in one portion. The solution was agitated to ensure complete reaction. The resulting mixture then was added to the previously prepared mixed anhydride solution. The resulting mixture was stirred at −15° C. for four hours. The mixture then was allowed to slowly warm to room temperature, and stirring was continued overnight. The mixture then was poured onto 1 N sodium bicarbonate, and the resulting aqueous solution was extracted with ethyl acetate. The organic phase was separated and extracted successively with water, 1.5 N citric acid, and water. The ethyl acetate then was dried over magnesium sulfate and concentrated in vacuo to an oil (1.6 grams). The oil was dissolved in acetone and applied to two preparative thin layer plates. The plates were eluted with a 9:1 mixture of chloroform and methanol. The major component was cut from the TLC plates and eluted from the silica gel to give 0.8 grams (39%) of the title compound.

K.
N$^\alpha$-Methyl-L-tyrosyl-D-alanyl-glycyl-L-(N$^\alpha$-cyclopropylmethyl)-m-bromophenylalanine Amide, Acetate Salt To 15 ml. of TFA containing 3 ml. of anisole were added 0.8 grams (1.2 mmoles) of the product from Part J. The mixture was stirred at 0° C. for 30 minutes after which it was freeze-dried. The resulting solid was dissolved in 9.0 ml. of a 0.1 M ammonium acetate solution containing 31% acetonitrile. The solution was applied to a 4×72 cm. C$_{18}$ reverse phase silica gel HPLC column. The column was run at 60 psig pressure, and the eluate was monitored at 280 nm. The appropriate fractions were combined and lyophilized. The resulting solid was dissolved in 0.2 M acetic acid (10 ml.), and the solution was applied to a 2.5×100 cm. column of G-10 Sephadex which had been previously equilibrated with the same solvent. The eluate was monitored at 280 nm, and the appropriate fractions were combined and lyophilized to give 773 mg. (97%) of the title compound.

$[\alpha]_D^{25}$ +6.64 (c=0.5, 1 N HCl).

Analysis, calculated for C$_{30}$H$_{40}$N$_5$O$_7$Br (662.6): C, 54.38; H, 6.09; N, 10.57. Found: C, 54.30; H, 5.99; N, 10.28.

Amino Acid Analysis: Ala, 0.97; Gly, 1.03; NH$_3$, 0.99.

Other compounds that have been prepared using the procedure of Example 1 include the following:

EXAMPLE 2
—L-(N-Methyl)tyrosyl-D-alanyl-glycyl-L-(N-ethyl)-m-bromophenylalanine Amide, Acetate Salt $[\alpha]_D^{25}$ +7.1° (c=0.5, 1 N HCl).

Analysis, calculated for C$_{28}$H$_{38}$N$_5$O$_7$Br (636.5): C, 52.83; H, 6.02; N, 11.00. Found: C, 53.09; H, 6.13; N, 11.18.

Amino Acid Analysis: Ala, 0.99; Gly, 1.01; NH$_3$, 1.04.

EXAMPLE 3
—L-Tyrosyl-D-alanyl-glycyl-L-(N-ethyl)-m-bromophenylalanine Amide, Acetate Salt $[\alpha]_D^{25}$ −8.3° (c=0.5, 1 N HCl).

Analysis, calculated for C$_{27}$H$_{36}$N$_5$O$_7$Br (623): C, 52.09; H, 5.83; N, 11.25. Found: C, 52.13; H, 6.09; N, 11.39.

Amino Acid Analysis: Tyr, 1.01; Ala, 0.99; Gly, 0.99; NH$_3$, 1.01.

EXAMPLE 4
—L-(N-Methyl)tyrosyl-D-alanyl-glycyl-L-(N-ethyl)-m-methyl-phenylalanine Amide, Acetate Salt $[\alpha]_D^{25}$ +9.2° (c=0.5, 1 N HCl).

Analysis, calculated for C$_{29}$H$_{41}$N$_5$O$_7$ (571.7): C, 60.93; H, 7.23; N, 12.25. Found: C, 60.68; H, 7.00; N, 12.46.

Amino Acid Analysis: Ala, 0.98; Gly 1.02; NH$_3$, 0.96.

EXAMPLE 5
—L-Tyrosyl-D-alanyl-glycyl-L-(N-ethyl)-m-chlorophenylalanine Amide, Acetate Salt.

$[\alpha]_D^{25}$ −13.7° (c=0.5, 1 N HCl).

Analysis, calculated for C$_{27}$H$_{36}$N$_5$O$_7$Cl (578.1): C, 56.10; H, 6.28; N, 12.12. Found: C, 55.84; H, 6.37; N, 12.35.

Amino Acid Analysis: Tyr, 1.02; Ala, 0.99; Gly, 0.98; NH$_3$, 0.88.

EXAMPLE 6
—L-(N-Methyl)tyrosyl-D-alanyl-glycyl-L-(N-ethyl)-m-chlorophenylalanine Amide, Acetate Salt $[\alpha]_D^{25}$ −9.2° (c=0.5, 1 N HCl).

Analysis, calculated for C$_{28}$H$_{38}$N$_5$O$_7$Cl (592.1): C, 56.80; H, 6.47; N, 11.83. Found: C, 57.11; H, 6.45; N, 12.15.

Amino Acid Analysis: Ala, 0.99; Gly, 1.00; NH$_3$, 1.01.

EXAMPLE 7
—L-Tyrosyl-D-alanyl-glycyl-L-(N-ethyl)-m-iodophenylalanine Amide, Acetate Salt $[\alpha]_D^{25}$ −14.0° (c=0.5, 1 N HCl).

Analysis, calculated for C$_{27}$H$_{36}$N$_5$O$_7$I (669.5): C, 48.44; H, 5.42; N, 10.46. Found: C, 48.40; H, 5.25; N, 10.66.

Amino Acid Analysis: Tyr, 1.01; Ala, 0.99; Gly, 0.99; NH$_3$, 1.05.

The analgesic activity of the compounds of this invention is demonstrated by the mouse hot plate test. In this test, an upright acrylic cylinder comprising, as its base, a hot plate surface which is maintained at 52° C. is used. A mouse is given, by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measured. An agent which exhibits analgesic activity produces an increase in this latency over that of control mice which receive only the carrier. This must occur in a dose range which produces no motor incoordination or incapacitation. The following Table I records ED$_{50}$ results obtained from this test. By the term "ED$_{50}$" is meant that dose which produces analgesia in 50% of the mice tested. Analgesia is defined as a response latency in the presence of test compound that is equal to or greater than the control response latency plus two standard deviations. The percent analgesia data are converted to probits, and the ED$_{50}$ is calculated by regression analysis of the dose-response data. Each dose response curve must have at least four points, and each point is determined using data from a minimum of ten treated mice and ten control mice.

TABLE I

| Analgesic Activity, Hot Plate Test | |
|---|---|
| Compound | ED$_{50}$, mg./kg. |
| Example 1 | 1.2 × 10$^{-7}$ |
| Example 2 | 0.003 |
| Example 3 | 0.0049 |
| Example 4 | 0.003 |
| Example 5 | 0.0003 |
| Example 6 | 0.0018 |
| Example 7 | 0.0019 |

In addition, the compounds of this invention exhibit low physical dependence liability. This is demonstrated by the mouse locomotor activity test. A high correlation has been established between the degree of physical dependence liability of a compound and its ability to elicit mouse locomotor activity; Cf. Goldstein et al., *The Journal of Pharmacology and Experimental Therapeutics* 169, 175–184 (1969); Rethy et al., *The Journal of Pharmacology and Experimental Therapeutics* 176, 472–479 (1971); and Brase et al., *The Journal of Pharma-* cology and Experimental Therapeutics 201(2), 368–374 (1977).

Mouse locomotor activity is measured using cylindrical cages of wire mesh 2 inches high and 11 inches in diameter. Six cages are enclosed in a ventilated, sound-attenuated chamber having uniform lighting. A light beam is passed through the center of the cage to a photocell on the opposite side. Two mice are placed in each cage for one hour to become acclimated to the surroundings. Five pairs of mice then are injected subcutaneously with a predetermined dose of the test compound, the remaining pair receiving saline carrier free of test compound. The mice are returned to their respective cages for three hours. The number of counts per each 15 minute period as well as the total number over the three hour period are recorded. Each interruption of the light beam constitutes a count.

The following Table II reflects a mean of the total counts for each group of ten mice tested using a particular compound and dose level. It is apparent, relative to related prior art compounds, that the compounds of the invention exhibit substantially reduced locomotor activity.

TABLE II

| R—Tyr—D—Ala—Gly—(N—R$_1$) (R$_2$)Phe—NH$_2$ | | | | | | | |
|---|---|---|---|---|---|---|---|
| Compound | | | Dose, mg./kg. | | | | |
| R | R$_1$ | R$_2$ | 4 | 8 | 16 | 32 | 64 | 128 |
| H | Et | m-Cl | 125 | 613 | 819 | 2388 | 3667 | 2807 |
| Me | Et | m-Cl | 148 | 304 | 796 | 1978 | 4477 | 3476 |
| H | Et | m-Br | — | 200 | 512 | 1092 | 2820 | — |
| Me | Et | m-Br | 142 | 235 | 358 | 701 | 2523 | 5153 |
| Me | Cpm | m-Br | 171 | 140 | 276 | 320 | 1888 | 2159 |
| H | Et | m-I | 178 | 174 | 363 | 852 | 1630 | 2871 |
| Me | Et | m-Me | 173 | 255 | 537 | 1176 | 3231 | 3852 |
| H | Et | H | 704 | 1204 | 2916 | 3528 | — | — |
| Me | Et | p-F | 431 | 1425 | 2415 | 2033 | — | — |

We claim:
1. A compound of the formula

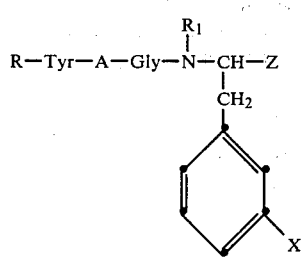

and pharmaceutically acceptable non-toxic acid addition salts thereof, in which
R is hydrogen, methyl, ethyl, cyclopropylmethyl, or allyl;
A is a residue of a D-amino acid selected from the group consisting of Ala, Abu, Nva, Val, Nle, Leu, Ile, Gly(Al), Gly(Cp), Met, Cys(Me), Met(O), Cys(Me) (O), Ser, Thr, and Hse;
R$_1$ is C$_1$–C$_3$ primary alkyl, cyclopropylmethyl, allyl, ethylthiomethyl, 2-fluoroethyl, or propargyl;
X is bromo, iodo, chloro, methyl, trifluoromethyl, or methoxy; and
Z is —CH$_2$OR$_2$,

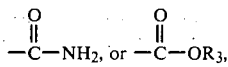

in which R$_2$ is hydrogen, acetyl, or acetoxymethyl and R$_3$ is C$_1$–C$_3$ alkyl.

2. Compound of claim 1, in which R is hydrogen.
3. Compound of claim 2, in which Z is

4. Compound of claim 3, in which X is bromo or iodo.
5. Compound of claim 4, in which R$_1$ is C$_1$–C$_3$ primary alkyl, cyclopropylmethyl, allyl, or propargyl.
6. Compound of claim 5, in which A is Ala, Abu, Nva, Val, Nle, Leu, Ile, Ser, Thr, or Hse.
7. Compound of claim 6, in which A is Ala, Abu, Nva, Val, Nle, Leu, or Ile.
8. Compound of claim 7, in which A is Ala.
9. Compound of claim 8, in which R$_1$ is ethyl, cyclopropylmethyl, allyl, or propargyl.
10. Compound of claim 9, in which R$_1$ is ethyl.
11. Compound of claim 10, in which X is bromo.
12. Compound of claim 10, in which X is iodo.
13. Compound of claim 9, in which R$_1$ is cyclopropylmethyl.
14. Compound of claim 13, in which X is bromo.
15. Compound of claim 13, in which X is iodo.
16. Compound of claim 3, in which X is chloro.
17. Compound of claim 16, in which A is Ala.
18. Compound of claim 17, in which R$_1$ is ethyl, cyclopropylmethyl, allyl, or propargyl.
19. Compound of claim 18, in which R$_1$ is cyclopropylmethyl.
20. Compound of claim 18, in which R$_1$ is ethyl.
21. Compound of claim 1, in which R is methyl.
22. Compound of claim 21, in which Z is

23. Compound of claim 22, in which X is bromo or iodo.
24. Compound of claim 23, in which R$_1$ is C$_1$–C$_3$ primary alkyl, cyclopropylmethyl, allyl, or propargyl.
25. Compound of claim 24, in which A is Ala, Abu, Nva, Val, Nle, Leu, Ile, Ser, Thr, or Hse.
26. Compound of claim 25, in which A is Ala, Abu, Nva, Val, Nle, Leu, or Ile.
27. Compound of claim 26, in which A is Ala.
28. Compound of claim 27, in which R$_1$ is ethyl, cyclopropylmethyl, allyl, or propargyl.
29. Compound of claim 28, in which R$_1$ is ethyl.
30. Compound of claim 29, in which X is bromo.
31. Compound of claim 29, in which X is iodo.
32. Compound of claim 28, in which R$_1$ s cyclopropylmethyl.
33. Compound of claim 32, in which X is bromo.
34. Compound of claim 32, in which X is iodo.
35. Compound of claim 22, in which X is chloro.
36. Compound of claim 35, in which A is Ala.
37. Compound of claim 36, in which R$_1$ is ethyl, cyclopropylmethyl, allyl, or propargyl.
38. Compound of claim 37, in which R$_1$ is cyclopropylmethyl.
39. Compound of claim 37, in which R$_1$ is ethyl.

* * * * *